United States Patent
Mrowka et al.

(10) Patent No.: US 9,449,530 B1
(45) Date of Patent: Sep. 20, 2016

(54) AUTOMATIC DIET TRACKING SYSTEM AND METHOD

(71) Applicant: Genesant Technologies, Inc., Vienna, VA (US)

(72) Inventors: James J. Mrowka, San Mateo, CA (US); Paola N. Robey, Falls Church, VA (US); Daniel S. Robey, Falls Church, VA (US); Athanasios G. Christ, Reston, VA (US)

(73) Assignee: GENESANT Technologies, Inc., Vienna, VA (US)

( * ) Notice: Subject to any disclaimer, the term of this patent is extended or adjusted under 35 U.S.C. 154(b) by 0 days.

(21) Appl. No.: 15/041,780

(22) Filed: Feb. 11, 2016

Related U.S. Application Data

(60) Provisional application No. 62/115,677, filed on Feb. 13, 2015, provisional application No. 62/193,879, filed on Jul. 17, 2015.

(51) Int. Cl.
*G06F 17/27* (2006.01)
*G06F 17/30* (2006.01)
*G09B 19/00* (2006.01)

(52) U.S. Cl.
CPC ....... *G09B 19/0092* (2013.01); *G06F 17/2705* (2013.01)

(58) Field of Classification Search
CPC .... G06F 17/27; G06F 17/20; G06F 17/2705; G06F 17/271; G06F 17/2715; G06F 17/272; G06F 17/2725; G06F 17/273; G06F 17/2735; G06F 17/274; G06F 17/2745; G06F 17/275; G06F 17/2755; G06F 17/276; G06F 17/2765; G06F 17/2795; G06F 19/00; G06F 19/3431; G06F 19/3475; G06F 17/30
USPC ................................................. 704/1, 9, 10
See application file for complete search history.

(56) References Cited

U.S. PATENT DOCUMENTS

| | | | |
|---|---|---|---|
| 7,076,438 B1 * | 7/2006 | Tobelmann | G06F 19/3475 128/921 |
| 8,690,578 B1 * | 4/2014 | Nusbaum | G09B 19/00 128/905 |
| 8,924,239 B1 * | 12/2014 | Kurple | G06F 19/3475 705/2 |
| 2002/0049736 A1 * | 4/2002 | Chow | G06Q 30/06 |
| 2002/0124017 A1 * | 9/2002 | Mault | A61B 5/222 600/300 |
| 2002/0156351 A1 * | 10/2002 | Sagel | A23L 1/293 600/300 |

(Continued)

*Primary Examiner* — Lamont Spooner
(74) *Attorney, Agent, or Firm* — Barry N. Young

(57) ABSTRACT

An automatic diet tracking system and methods comprising: i) voice-transcribed or typed text natural language processing and automatic tracking to record food, food quantity, and nutrition data, ii) multi-food administration to record multiple foods and related data in a single user voice-transcribed or typed text submission, and iii) location-based diet recommendations system that provides customized food recommendations to users based on user preferences and user physical location. Further, such automatic diet tracking system and location-based diet recommendations system are usable through computers, tablets, mobile phones, smart watches, wearables and other similar devices.

20 Claims, 12 Drawing Sheets

(56) References Cited

U.S. PATENT DOCUMENTS

| | | | |
|---|---|---|---|
| 2004/0138820 A1* | 7/2004 | Morris | G06F 19/3475 702/19 |
| 2004/0229195 A1* | 11/2004 | Marggraff | G06K 7/10881 434/169 |
| 2005/0010416 A1* | 1/2005 | Anderson | G06F 17/27 704/271 |
| 2005/0113650 A1* | 5/2005 | Pacione | A61B 5/411 600/300 |
| 2005/0121504 A1* | 6/2005 | Sanders | G06F 19/3406 235/87 A |
| 2008/0162352 A1* | 7/2008 | Gizewski | G06F 19/345 705/50 |
| 2008/0306347 A1* | 12/2008 | Deutsch | G06F 19/3418 600/300 |
| 2009/0099873 A1* | 4/2009 | Kurple | G06Q 50/24 705/3 |
| 2009/0216629 A1* | 8/2009 | James | G06F 19/3418 705/14.19 |
| 2009/0219159 A1* | 9/2009 | Morgenstern | A63B 24/00 340/573.1 |
| 2011/0061027 A1* | 3/2011 | Brown | G06F 17/30731 715/840 |
| 2011/0153744 A1* | 6/2011 | Brown | G06F 17/30731 709/204 |
| 2012/0110458 A1* | 5/2012 | Brown | G06F 17/30575 715/733 |
| 2012/0303638 A1* | 11/2012 | Bousamra | G06F 19/3475 707/751 |
| 2013/0138656 A1* | 5/2013 | Wheaton | G06F 17/30705 707/740 |
| 2013/0158367 A1* | 6/2013 | Pacione | E04F 13/06 600/301 |
| 2013/0216982 A1* | 8/2013 | Bennett | G09B 5/00 434/127 |
| 2014/0114889 A1* | 4/2014 | Dagum | G06F 19/3406 706/12 |
| 2014/0221791 A1* | 8/2014 | Pacione | A61B 5/7455 600/301 |
| 2015/0033290 A1* | 1/2015 | Benyo | H04L 67/34 726/3 |
| 2015/0112899 A1* | 4/2015 | Dagum | A61B 5/6898 706/12 |
| 2015/0149207 A1* | 5/2015 | O'Keefe | G06F 19/3456 705/3 |
| 2015/0216413 A1* | 8/2015 | Soyao | A61B 5/0022 709/204 |
| 2015/0242468 A1* | 8/2015 | Shoemaker | G06F 17/30528 707/755 |
| 2015/0272473 A1* | 10/2015 | Zafiroglu | A61B 5/682 600/302 |
| 2016/0012342 A1* | 1/2016 | Simon | G06N 5/048 706/52 |

* cited by examiner

AUTOMATIC DIET TRACKING SYSTEM AND METHOD

CROSS-REFERENCE TO RELATED APPLICATIONS

This application claims the benefit of U.S. Provisional Application No. 62/115,677, filed 13 Feb. 2015 and U.S. Provisional Application No. 62/193,879, filed 17 Jul. 2015, the disclosures of which are incorporated by reference herein.

BACKGROUND

Current diet tracking systems comprise software systems designed to run on mobile and other computing devices that are extremely tedious to use. These software systems all require a user to undergo the same lengthy process in which that user must: i) select breakfast, lunch, dinner or snack for meal placement, ii) type or voice transcribe (using the device microphone) the food name, iii) search for the food, iv) select the appropriate food from a long list of options, v) confirm or edit the food quantity and the quantity unit, and then repeat for every food in the meal to be tracked.

Importantly, to demonstrate the gross inefficiency of the aforementioned diet tracking systems one simply needs to add up the current number of steps required of users in order to track a five food meal. That number, without using any recent foods tracked data, is an astounding thirty-five steps. This is burdensome and inconvenient which detracts from the use of such systems. Further, current art that has not been applied in functional systems, while conceptualizing some limited automation to the diet tracking process if, and only if, a fuzzy search text match is found, also falls grossly short in providing any practical amount of efficiency improvement and food tracking accuracy for users.

It is desirable to provide systems and methods that address the foregoing and other problems with known approaches, and it is to this that the present invention is directed. For the sake of clarity, diet tracking can be defined as the process of logging an individual user's food eaten (e.g. spaghetti), including the associated food quantity (e.g. 1, 2, 3, etc.) and quantity unit (e.g. cup, ounce, etc.) and nutrition information for such food (e.g. 221 calories, 1 gram of fat, 43 grams of carbohydrates, 3 grams of fiber, etc.).

SUMMARY OF THE INVENTION

The invention described herein relates to an automatic diet tracking system and method. It is an object of the present invention to provide a comprehensive automatic diet tracking system and method that are significantly faster and more efficient to use than the current art is able to deliver. This is achieved by the invention through the automation of the complete diet tracking process. The current art is incapable of such complete automation and these systems require manual user input throughout much or all of the diet tracking experience.

The diagrams and detailed description contained herein below provide a step by step look at the methods, algorithms and processes of the invention that enable automatic diet tracking. However, this summary will provide a general overview of such methods, algorithms and processes with the details left to the detailed description of preferred embodiments below.

The present invention receives user-submitted input text describing food such as by voice-transcribed or typed text and parses the input text into segments of parsed text. The food quantity (e.g. 1, 2, 3, etc.), if any, is removed from the parsed text and a multi-path unit database search may be done on the text to find a quantity unit (e.g. cup, ounce, etc.). If a unit is found, it is tracked by the system along with the food quantity. If the parsed text does not contain a food quantity the system may assume a predetermined quantity of one (1).

The remaining parsed text is cleaned and a sequence of a user data history lookup and then an entire user population data history lookup may be performed, as necessary, to identify previous text match data to determine what food (F) should be tracked by the system. If no previous text matches are found, the system modifies the search strings for the parsed and cleaned text and then runs a food database search on such text. An entire user population data history lookup may be performed to find the total number of times each food search result has been tracked by the system, and that data along with a food search score may be used in multi-rule process that results in a food text match scoring rank. The top ranked food may be selected as the food (F) tracked by the system.

If the parsed text does not contain a quantity unit (e.g. cup, ounce, etc.), then a user data history lookup followed by an entire user population data history lookup may be done, as necessary based on a multi-path process, to use previous quantity unit data associated with the food (F) identified to be tracked to determine what unit should be tracked by the system.

The invention utilizes machine learning with large, real-time user data sets, text aliasing logic and data that replaces certain text with aliased text that is appropriate (e.g. oaks=oats; like=light; three=3), and quantity exceptions logic and data (Eleven, 12 inch, etc.) as part of the processes of enabling complete automatic diet tracking.

The aforementioned innovative processes enable the invention to provide automatic diet tracking for all diet information submissions, including submissions that do not include a food quantity and/or a quantity unit. This results in a vastly superior diet tracking experience over the current art. Users need only the single diet information submission for complete automatic diet tracking of one or more foods and/or meals. The resulting efficiency provided to users of the invention enables them to track a five food meal in only three steps, compared to the thirty-five steps required by the current art in diet tracking systems.

Further, the location-based diet recommendations system uses user geographic location, diet tracking data and weight loss plan derived nutrient targets to provide customized, location-aware food and/or meal recommendations to the user in real-time.

BRIEF DESCRIPTION OF THE DRAWINGS

In the course of the detailed description below, reference will be made to the attached drawings. These drawings illustrate different objects, aspects and advantages of the present invention, and also include reference numbers designating structures, components and elements present in the various embodiments illustrated. It is understood that various combinations of the structures, components and/or elements other than those specifically shown are also contemplated and are within the scope of the present invention.

Moreover, there are a number of different embodiments described and illustrated herein. The present invention is neither limited to any single aspect and/or embodiment, nor to any combinations and/or permutations of such aspects and/or embodiments. Moreover, each of the various aspects of the present invention, and/or embodiments thereof, may be employed alone or in combination with one or more of the other aspects and/or embodiments. For the sake of brevity, not all of the possible permutations and combinations are discussed and/or illustrated separately herein.

DETAILED DESCRIPTION OF PREFERRED EMBODIMENTS

Figure 1:
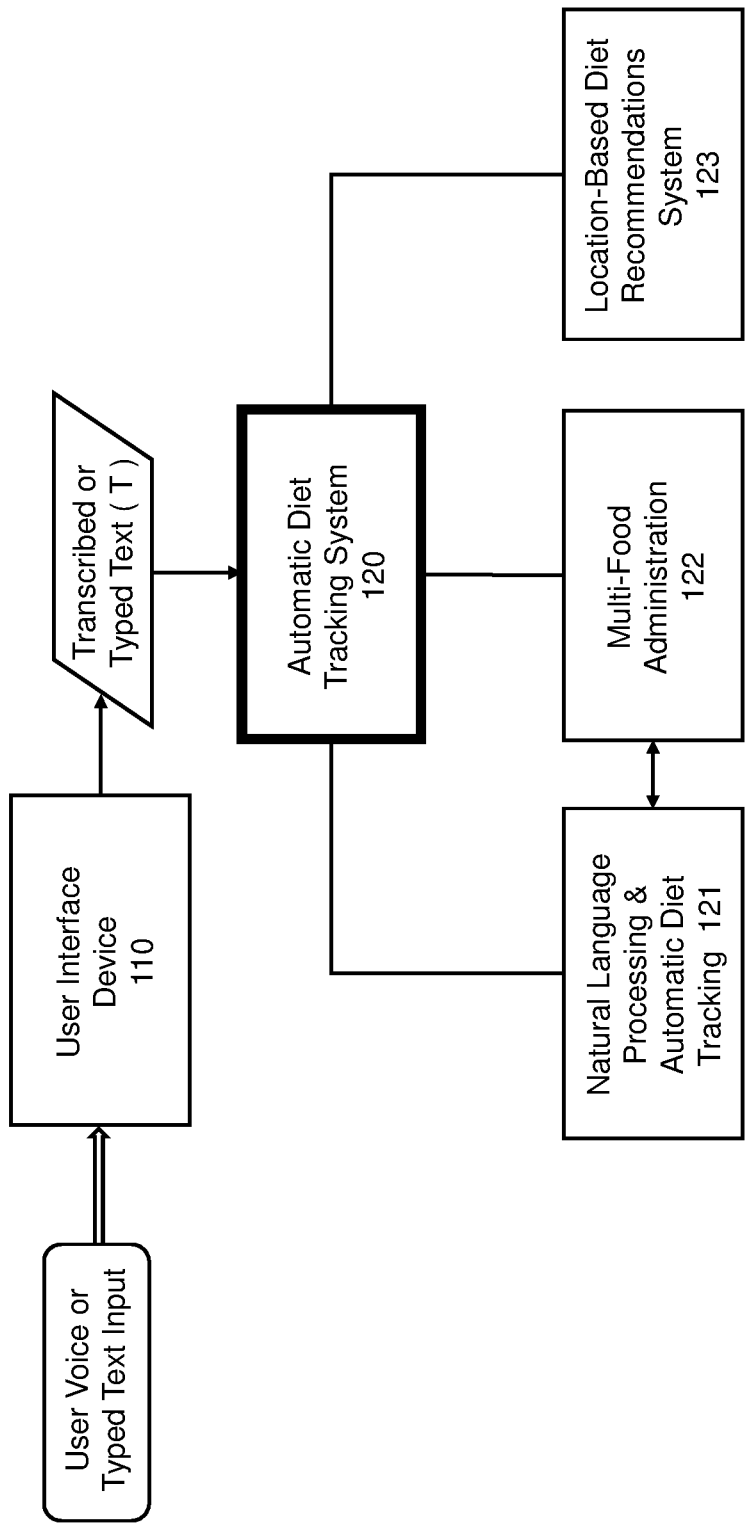
FIG. 1 is a block diagram of the architecture of a diet tracking system in accordance with a preferred embodiment of the invention.

In a preferred embodiment of the invention, a diet tracking system in accordance with the invention may be integrated with a mobile phone, tablet, laptop, desktop, smartwatch, wearable device or other computing system. FIG. 1 is a block diagram showing the top-level architecture of the automatic diet tracking system which illustrates that a user of the system inputs food tracking information as input text via voice or typed text into the user interface device 110, which may be associated with a mobile phone, tablet, laptop, desktop, smartwatch, wearable device or other computing system that comprises an automatic diet tracking system 120 in accordance with the invention. The system may comprise a processor and executable instructions embodied in computer readable media (not shown explicitly) for controlling the processor to perform the operations described herein, and may have associated data storage, also not shown. For voice inputs, the user interface device 110 may transcribe the voice input to produce text (T). Text (T) may also be input manually as typed text by a user via a user interface device 110. The voice-transcribed or typed text (T) enters the automatic diet tracking system 120. Voice-transcribed or typed text (T) from the diet tracking system 120 may be provided to a multi-food administration component 122 and to a natural language processing and automatic diet tracking component 121 for processing. Lastly, FIG. 1 shows the location-based diet recommendations component 123 that the user may access via the automatic diet tracking system user interfaces.

Figure 2:
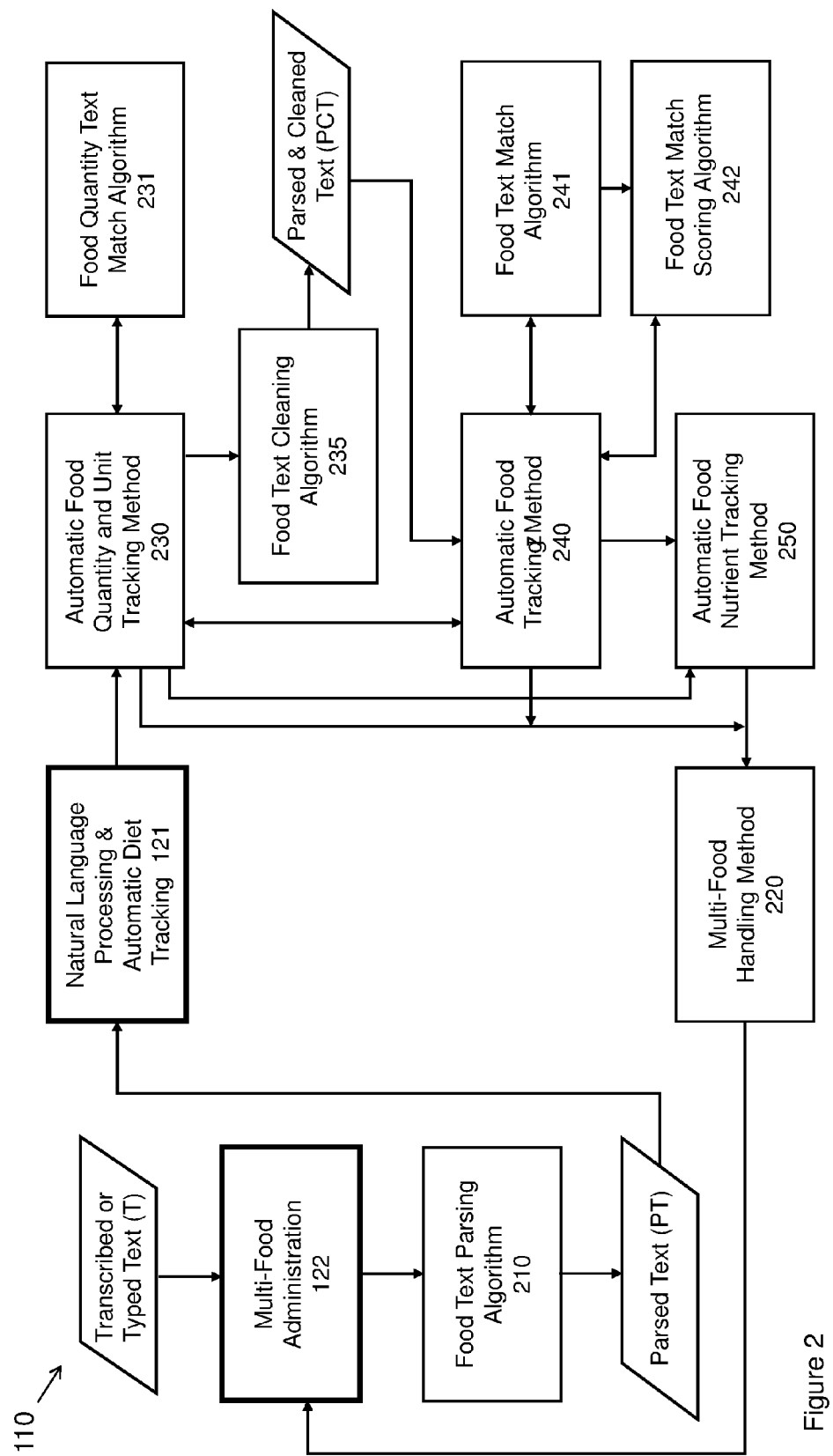
FIG. 2 is a block diagram of the architecture of an embodiment of a multi-food administration and natural language processing and automatic diet tracking system shown in FIG. 1.

FIG. 2 is a block diagram showing the architecture of an embodiment of the multi-food administration component 122 and the natural language processing and automatic diet tracking component 121, and illustrates how voice-transcribed or typed input text (T) enters and is processed therein. The voice-transcribed or typed text (T) first is provided to the multi-food administration component and is processed by the food text parsing algorithm 210, which then delivers parsed text (PT) to the natural language processing and automatic diet tracking component 121. The natural language processing and automatic diet tracking component 121 may first process the parsed text (PT) using an automatic food quantity and unit tracking method 230, which utilizes a food quantity text match algorithm 231 (described below), to produce the food quantity and a unit to be tracked for each food in the applicable parsed text (PT). The parsed text (PT) is stripped of any food quantity numeric value (QN) and food quantity unit (QU) found by the food quantity and unit tracking method 230, and the resulting parsed text (PT) without QN and QU ($PT_{WNU}$) may be delivered to a food text cleaning algorithm 235. The food text cleaning algorithm 235 generates parsed and cleaned text (PCT) for each segment of $PT_{WNU}$ and passes each such segment of PCT into an automatic food tracking method 240. The automatic food tracking method 240, which utilizes the food text match algorithm 241 and the food text match scoring algorithm 242 (described below), produces the food (F) to be tracked by the system for each segment of parsed and cleaned text (PCT) and then passes such food (F) back to an automatic food quantity and unit tracking method 230 for use therein in completion of its processes. Each generated food and associated food quantity and unit are then passed to an automatic food nutrient tracking method 250 which attaches applicable nutrition data to each such food and food quantity and unit. Each food name and associated food quantity and unit and applicable nutrition data are sent to a multi-food handling method 220, which keeps all foods and related data organized and properly associated with the proper segments of the parsed text (PT) for food quantity and unit and parsed and cleaned text (PCT) for food name for delivery back to the user interface device 110. The multi-food handling method 220 may be part of the multi-food administration component 122.

Figure 3:
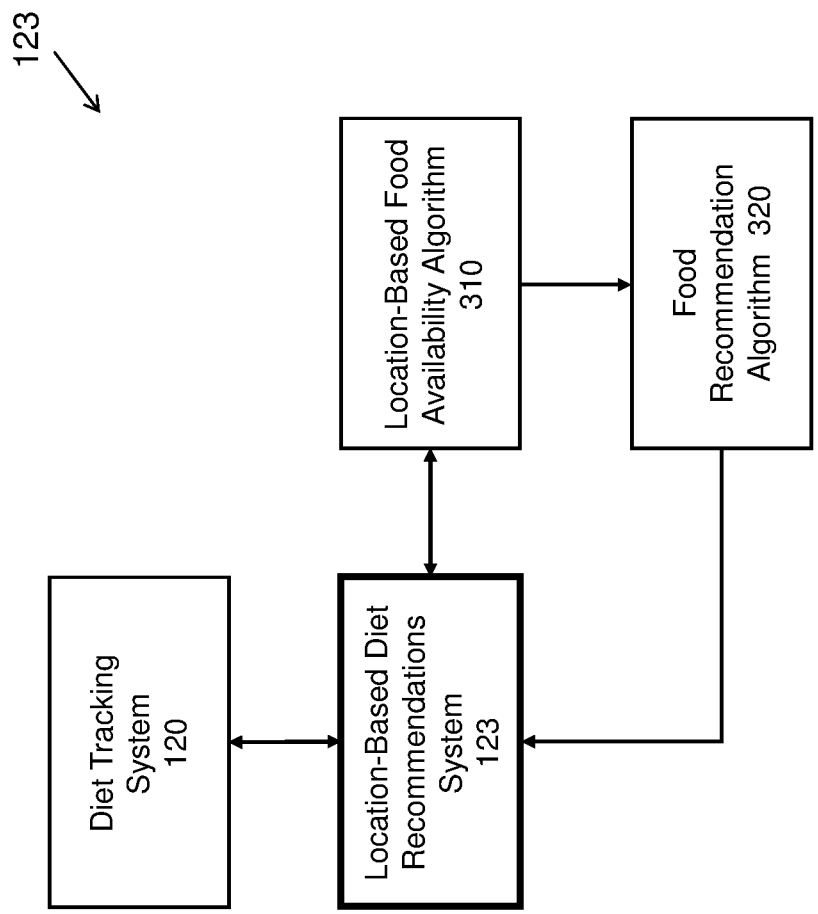
FIG. 3 is a block diagram of the architecture of an embodiment of a locations-based diet recommendations system shown in FIG. 1.
Figure 10:
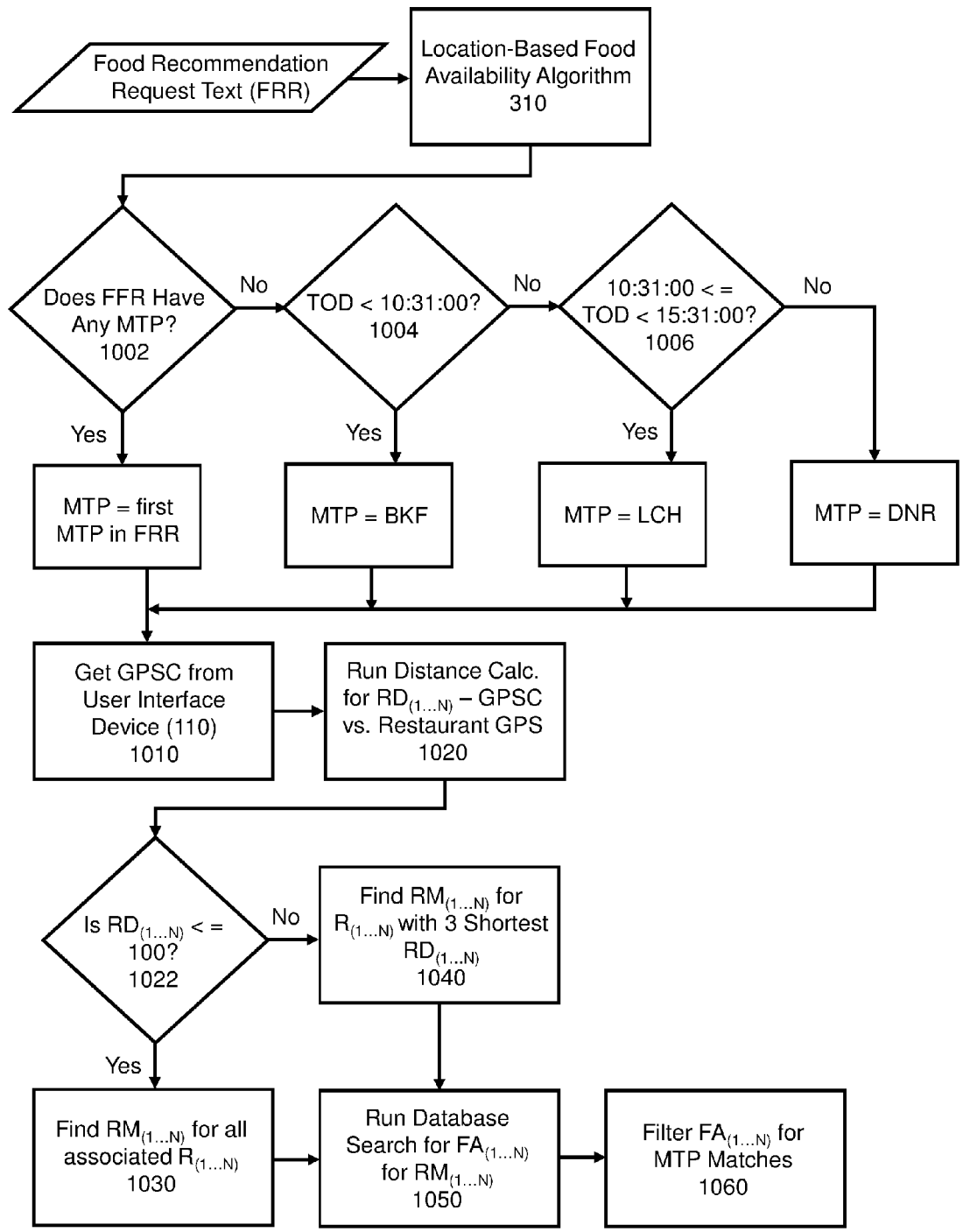
FIG. 10 is a flow diagram showing the steps performed by an embodiment of a location-based food availability algorithm shown in FIG. 3.
Figure 11:
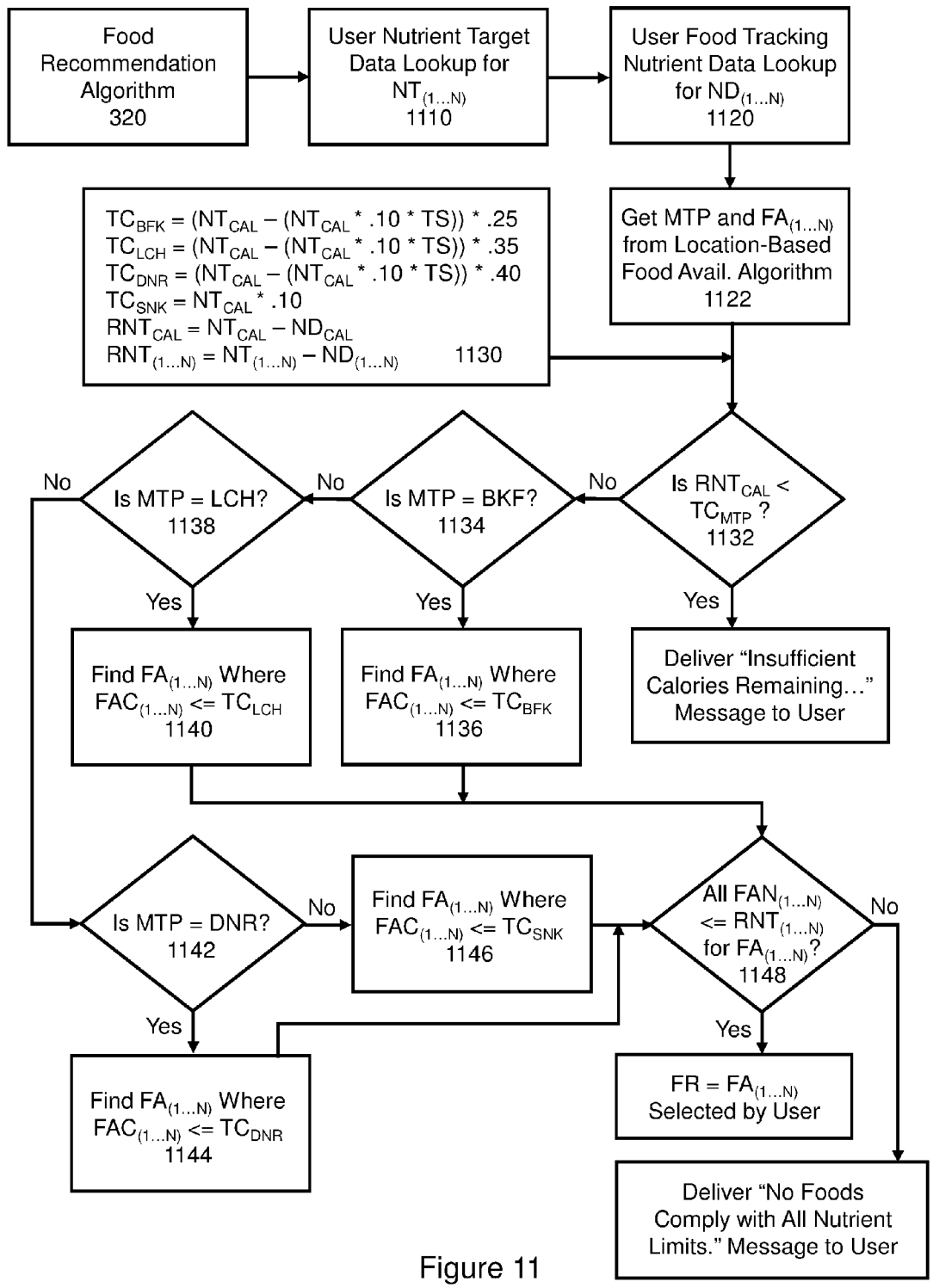
FIG. 11 is a flow diagram showing the steps performed by an embodiment of a food recommendation algorithm shown in FIG. 3.

FIG. 3 is a block diagram showing the architecture of an embodiment of a location-based diet recommendations system 123, and an associated location-based food availability algorithm 310, shown in FIG. 10, and a food recommendation algorithm 320, shown in FIG. 11, which are described below in detail.

Figure 4:
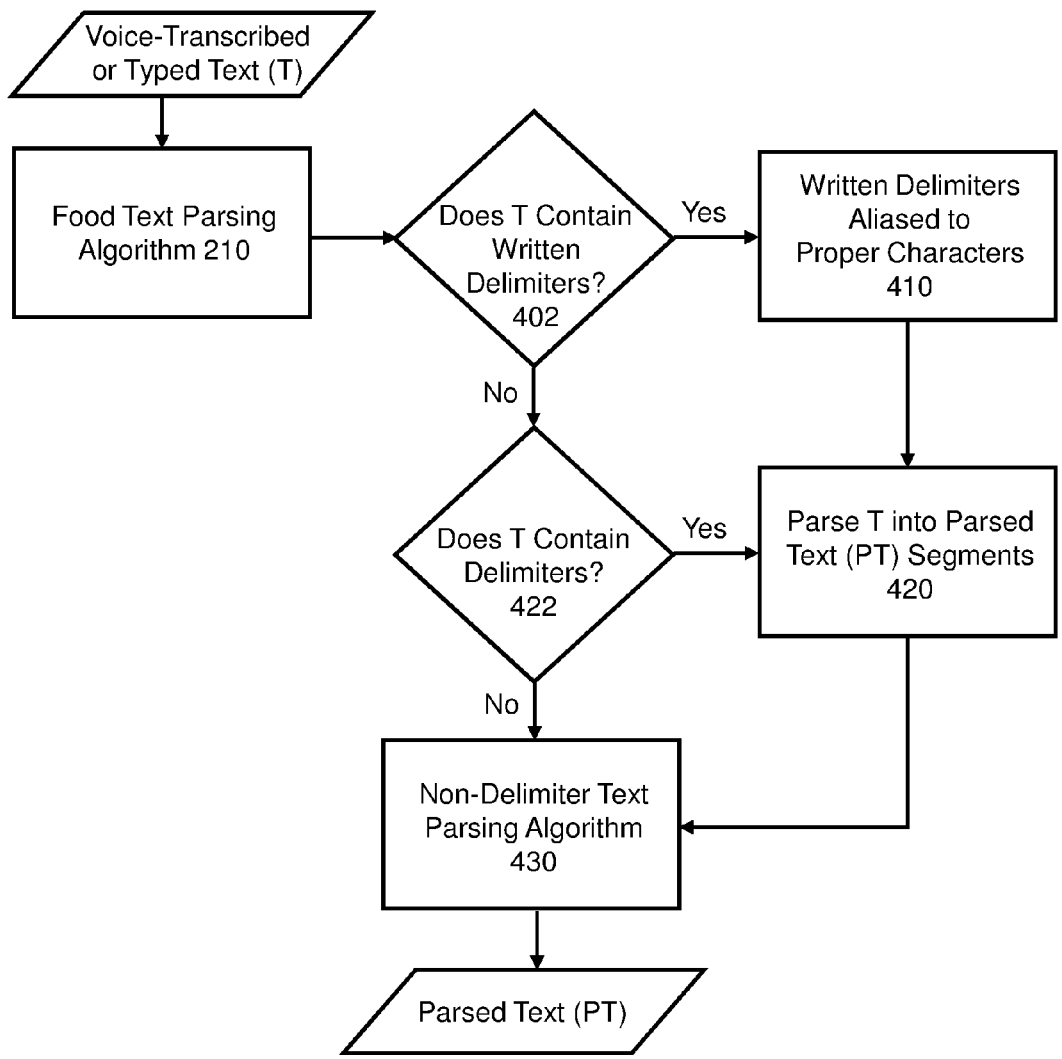
FIG. 4 is a flow diagram showing the steps performed by an embodiment of a food text parsing algorithm shown in FIG. 2.

FIG. 4 is a flow diagram showing the steps performed by an embodiment of the food text parsing algorithm 210 shown in FIG. 2. The purpose of the food text parsing algorithm 210 is to produce parsed text (PT) from the voice-transcribed or typed text (T). FIG. 4 shows that the voice-transcribed or typed text (T) may be first analyzed to determine at 402 if any written delimiters (e.g. "comma", "semi-colon", etc.) are found; if present, such written delimiters are aliased to proper characters (e.g. ",", ";") in process 410 of FIG. 4 and then the voice-transcribed or typed text (T) is parsed into parsed text (PT) segments in process 420 of FIG. 4. If written delimiters are not found in the text, the algorithm determines at 422 if any character delimiters are present; if character delimiters are found, then the voice-transcribed or typed text (T) is parsed into parsed text (PT) segments in process 420 of FIG. 4. The parsed text (PT) segments created in process 420 of FIG. 4 are then delivered into a non-delimiter text parsing algorithm 430 (described herein below) for further parsing, if any. If character delimiters are not found, then the voice-transcribed or typed text (T) is delivered to the non-delimiter text parsing algorithm 430. The non-delimiter text parsing algorithm 430 outputs the fully processed segments of parsed text (PT) for all parsed text (PT) segments and voice-transcribed or typed text (T) that have been inputted therein.

The following is a description of a preferred embodiment of the food text parsing algorithm 210:
  i. If T contains written delimiters (e.g. "comma", "semi-colon", etc.), Then alias written delimiter to the proper character (e.g. ",", ";");
    If T contains one or more delimiters (including aliased delimiters), Then parse T as specified by such delimiters into PT segments and run such PT segments through the non-delimiter text parsing algorithm to produce additional PT segments, if any;
    Else, run T through the non-delimiter text parsing algorithm to produce one or more PT segments.
  ii. Definitions of terms in the foregoing food processing algorithm 210 are:
    a. T=user-submitted voice-transcribed or typed input text
    b. PT=T that has been parsed into one or more parsed text segments The following is a description of an embodiment of the non-delimiter text parsing algorithm 430:
  i. If T contains more than one word,
    Then the Viterbi algorithm processes T, utilizing TMD to produce $VP_{(1 \ldots N)}$;
    If $VP_1$ is higher ranked than T, then each such $VP_1$ is a PT;
    Else, T=PT.
    Else, T=PT.
    If PT contains more than one word and one or more DW,
    Then the Viterbi algorithm processes PT, utilizing TMD to produce $VP_{(1 \ldots N)}$;
    If $VP_1$ is higher ranked than PT, then each segment of such $VP_1$ is a PT;
    Else, PT=PT.
    Else, PT=PT.
  ii. Definitions in this algorithm are:
    a. T=user-submitted voice-transcribed or typed text
    b. PT=T that has been parsed into one or more parsed text segments
    c. TMD=user and entire user population data history for PT matches
    d. $VP_{(1 \ldots N)}$=each Viterbi parse, where $VP_1$ is the top ranked (most likely) parse for any given T or PT
    e. DW=delimiting words, including "with", "and" and "or"

Figure 5A:
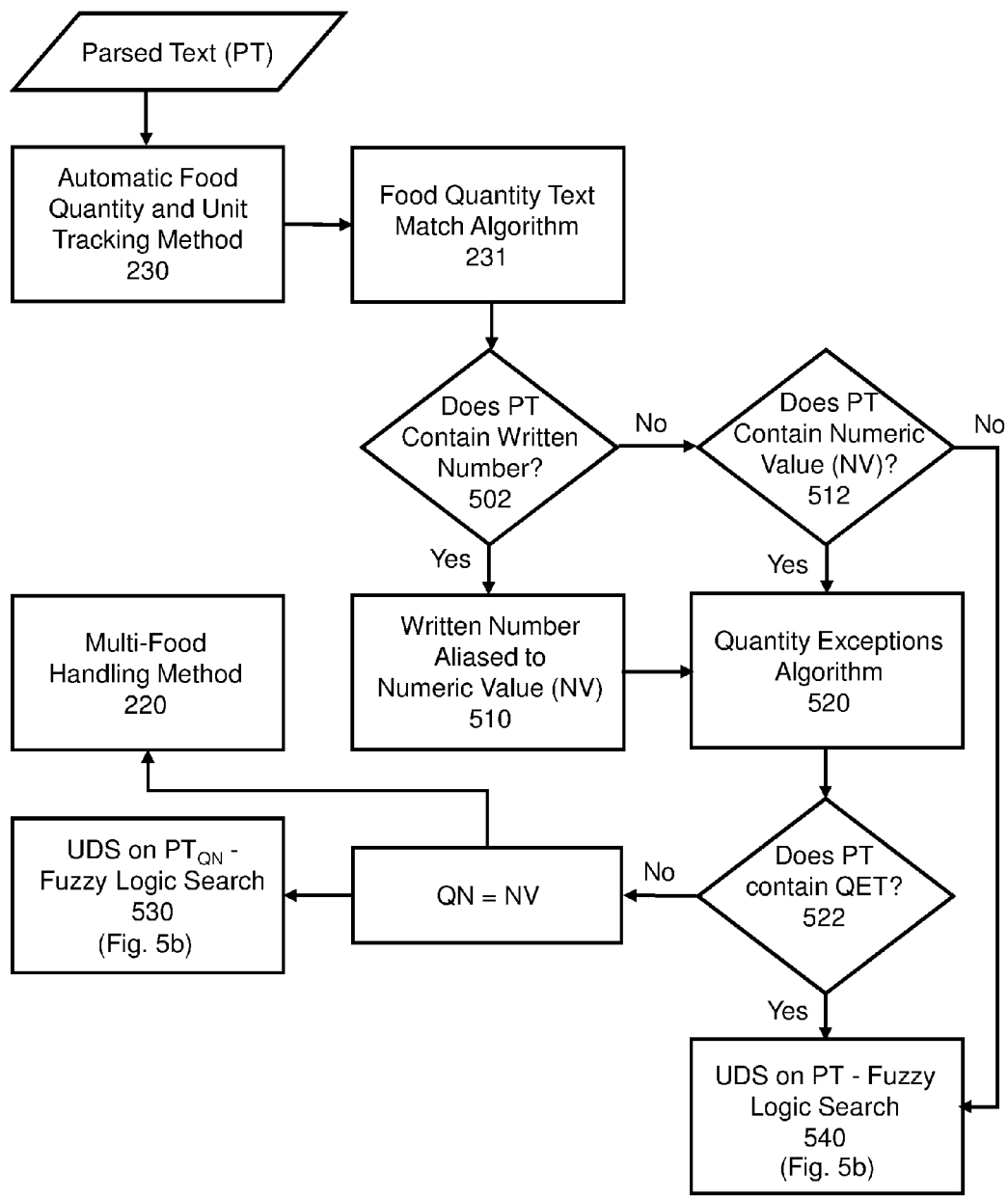
FIG. 5a is a flow diagram showing the first steps performed by an embodiment of an automatic food quantity and unit tracking method, including a food quantity text match algorithm, shown in FIG. 2.

FIG. 5a is a flow diagram showing the first steps that may be performed by the automatic food quantity and unit tracking method 230, including the food quantity text match algorithm 231, shown in FIG. 2. The purpose of the automatic food quantity and unit tracking method 230 is to find and track the food quantity and unit for the food in each parsed text (PT) segment. FIG. 5a shows that the food quantity text match algorithm 231 first determines at 502 whether parsed text (PT) contains a written number; if a written number is found, such written number(s) is aliased to the proper numeric value (NV) in process 510 of FIG. 5a. If a written number is not present, then the algorithm determines at 512 if a numeric value (NV) is present. If a numeric value (NV) is not found, then a fuzzy logic unit database search (UDS) 540 may be run, using text aliasing (e.g. "Grammys" equals "grams"), to find a matching food quantity unit (QU) within the parsed text (PT). If a numeric value (NV) is found or a written number has been through the aliasing process 510 of FIG. 5a, then the parsed text (PT) may be processed using a quantity exceptions algorithm 520. If one or more quantity exception terms (QET) (e.g. 7-Eleven, 12 inch, etc.), including any written or numeric value forms (e.g. 7-11, twelve inch, 12", etc.), that contain NV is found, then the fuzzy logic unit database search (UDS) 540 may be run, using text aliasing, to find a matching quantity unit (QU) with the parsed text (PT). If a quantity exception term (QET) is not found at 522, then the food quantity numeric value (QN) is set equal to the numeric value (NV) in the parsed text (PT), the quantity numeric value (QN) is sent to the multi-food handling method 220, and the fuzzy logic unit database search (UDS) 530 may be run, using text aliasing (e.g. "Grammys" equals "grams"), to find a matching food quantity unit (QU) with the word directly after QN in the sequence of words in PT ($PT_{QN}$).

Figure 5B:
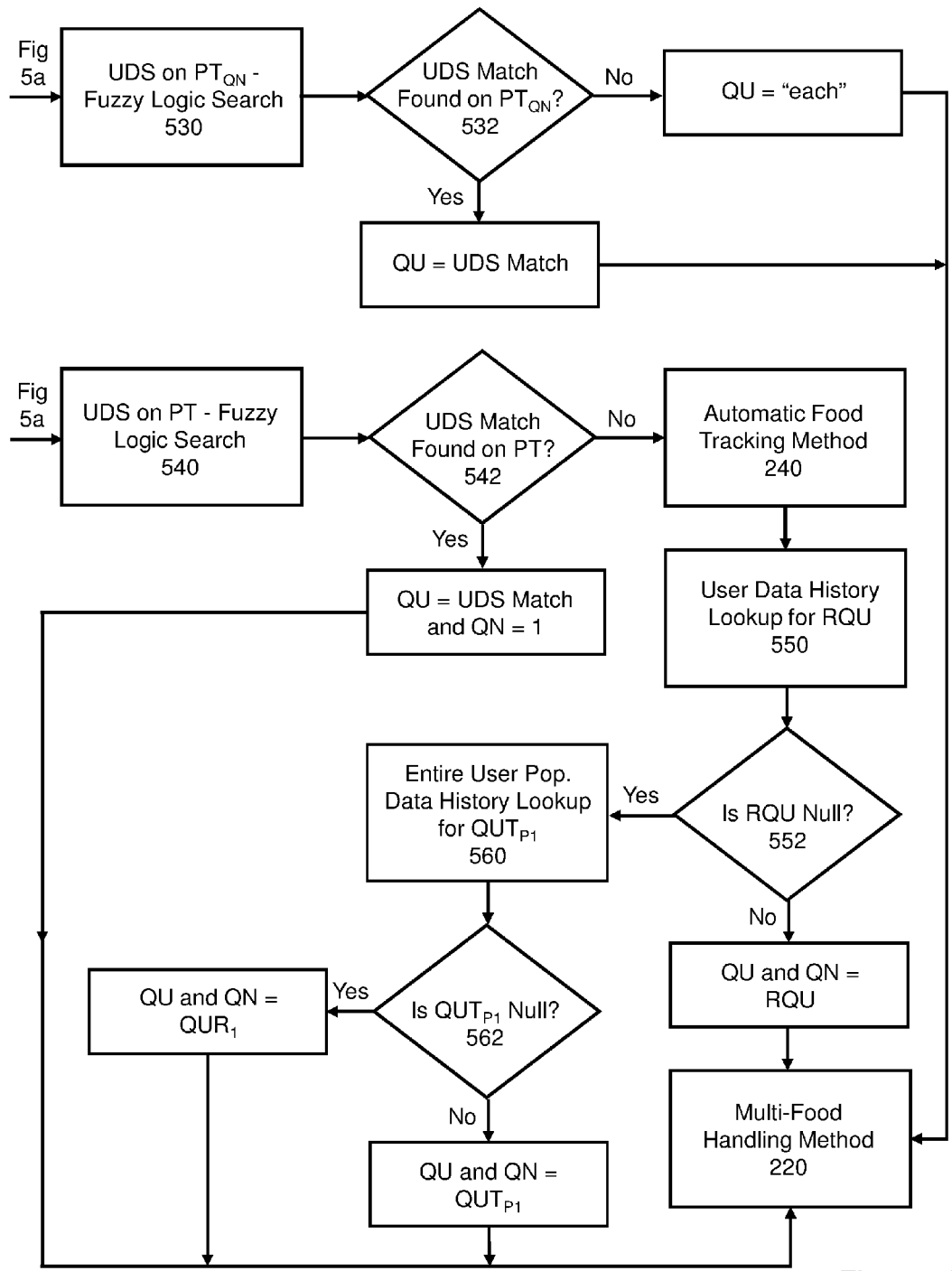
FIG. 5b is a flow diagram showing further steps performed by the automatic food quantity and unit tracking method, including the food quantity text match algorithm, shown in FIG. 2.

The following is a description of an embodiment of the quantity exceptions algorithm 520:
  i. Run database lookup for PT against QETL;
    If PT contains a QET, Then NV is not QN;
    Else, NV=QN.
  ii. Definitions of terms in this algorithm are:
    a. QET=a quantity exception term (e.g. 7-Eleven, 12 inch, etc.), including any written or numeric value forms (e.g. 7-11, twelve inch, 12", etc.), that contains a numeric value
    b. QETL=the list of all QET
    c. PT=user-submitted voice-transcribed or typed text that has been parsed by the food text parsing algorithm
    d. NV=a numeric value, including any aliased numeric value, found in PT
    e. QN=food quantity numeric value FIG. 5b is a continuation of the process flow diagram of FIG. 5a and shows further steps performed by the automatic food quantity and unit tracking method 230, including the food quantity text match algorithm 231, shown in FIG. 2. If a food quantity unit (QU) match is found at 532 from the unit database search (UDS) 530 on the word directly after QN in the sequence of words in the parsed text PT ($PT_{QN}$), then the food quantity unit (QU) is the UDS match; if no match is found, then the food quantity unit (QU) is equal to "each". The food quantity unit (QU) is then sent to the multi-food handling method 220. If a food quantity unit (QU) match is found at 542 from the unit database search (UDS) 540 on the parsed text (PT), then the food quantity unit (QU) is the UDS match, the food quantity numeric value (QN) is 1, and such food quantity unit (QU) and food quantity numeric value (QN) are sent to the multi-food handling method 220. If no match is found, then the automatic food tracking method 240 from FIG. 2 may be invoked to get the food to be tracked (F) for the resulting parsed and cleaned text (PCT) from such parsed text (PT). A user data history lookup for the most recently tracked food quantity unit (QU), and the most often associated QN for such QU, for the food to be tracked (F) by the user (RQU) 550 may be run, and if a RQU is found at 552, then the food quantity unit (QU) is such RQU and such food quantity unit (QU), and the most often associated QN for such QU, are sent to the multi-food handling method 220. If the user data history lookup for RQU is null at 552, then an entire user population history lookup for the food quantity unit (QU) tracked most often, and the most often associated QN for such QU, for the food to be tracked (F) by the entire user population ($QUT_{P1}$) 560 may be run; if $QUT_{P1}$ is found, then the food quantity unit (QU) is such $QUT_{P1}$ and such food quantity unit (QU), and the most often associated QN for such QU, are sent to the multi-food handling method 220. If the entire user population history lookup for $QUT_{P1}$ is null at 562, then the food quantity unit (QU) is set equal to the top ranking food quantity unit, and the most often associated QN for such QU, ($QUR_1$) for the food to be tracked (F) from the entire user population history lookup and such food quantity unit (QU), and the most often associated QN for such QU, are sent to the multi-food handling method 220.

Figure 6:
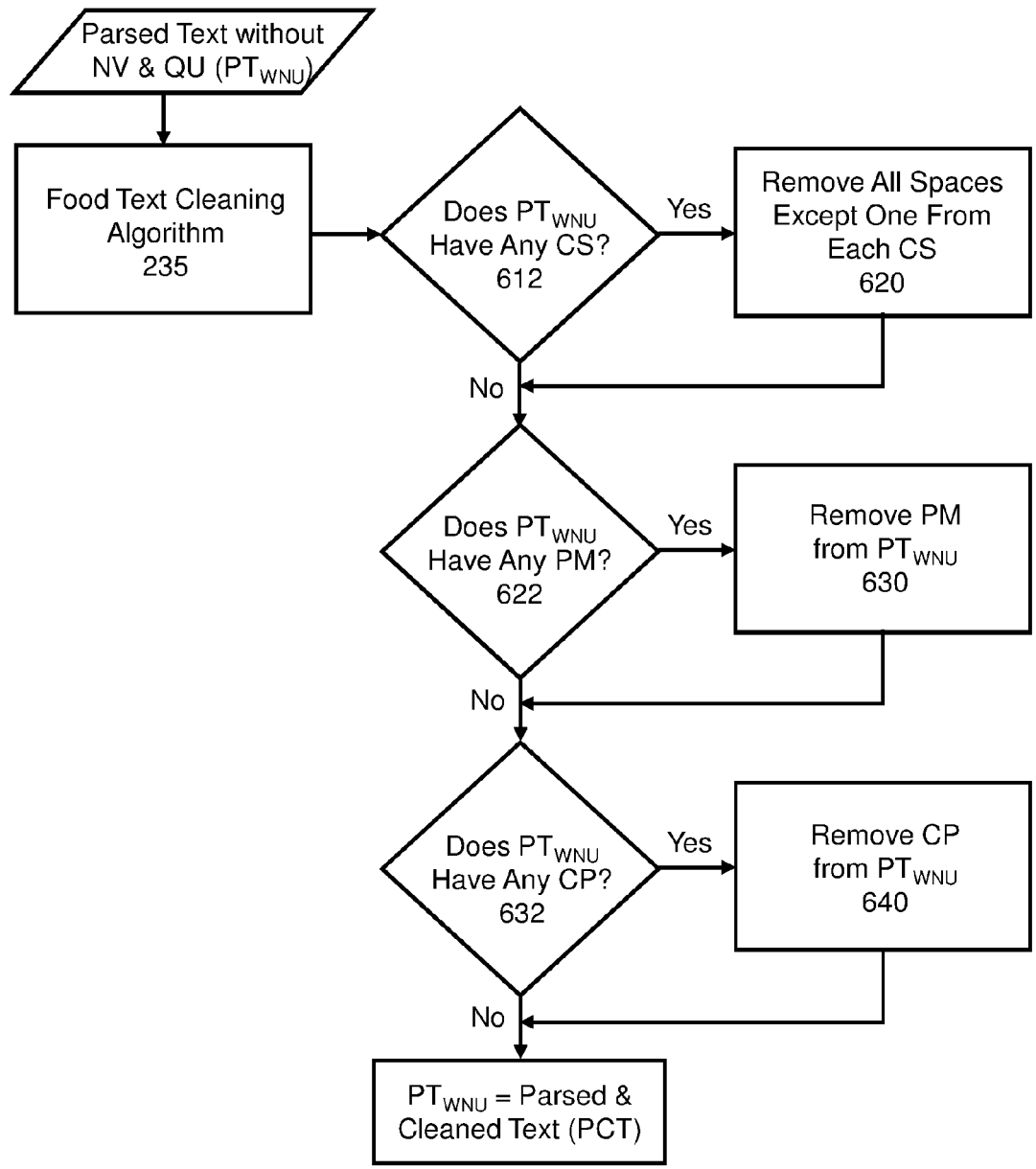
FIG. 6 is a flow diagram showing the steps performed by an embodiment of a food text cleaning algorithm shown in FIG. 2.

The following is a description of an embodiment of the food quantity text match algorithm 231:

i. If PT contains written number, Then alias written number to correct NV;
If PT contains NV (including aliased NV), Then run PT through the quantity exceptions algorithm;
If PT does not contain NV or if QET is not null, then perform UDS on PT;
  If UDS match found for PT, Then QU=UDS match and QN=1; Else, get F from automatic food tracking method;
  Run user data history lookup for RQU;
  QU and QN=RQU;
  If RQU is Null, Then run entire user population data history lookup for $QUT_{P1}$;
  QU and QN=$QUT_{P1}$;
  If $QUT_{p1}$ is Null, Then QU and QN=$QUR_1$.
If PT contains NV and QET is null, Then QN=NV and perform UDS on $PT_{QN}$ (fuzzy logic search using proprietary aliasing);
If UDS match found for $PT_{QN}$, Then QU=UDS match; Else QU="each".

ii. Definitions of terms are:
a. PT=user-submitted voice-transcribed or typed text that has been parsed by the food text parsing algorithm
b. NV=a numeric value, including any aliased numeric value, found in PT
c. QET=a quantity exception term (e.g. 7-Eleven, 12 inch, etc.), including any written or numeric value forms (e.g. 7-11, twelve inch, 12", etc.), that contains a NV
d. QU=food quantity unit
e. UDS=Unit database search, using proprietary aliasing, for matching QU
f. QN=food quantity numeric value
g. F=food to be tracked by system
h. $PT_{QN}$=the word directly after QN in the sequence of words in PT
i. RQU=most recently tracked QU, and most often associated QN for such QU, for F by user
j. $QUT_{P1}$=QU, and the most often associated QN for such QU, tracked most often for F by entire user population
k. $QUR_{(1 \ldots N)}$=all QU tracked for F by entire user population listed in ranked order (e.g. $QUR_1$ is the most often tracked quantity unit for F), and the most often associated QN for each such QU FIG. 6 illustrates the steps performed by a preferred embodiment of the food text cleaning algorithm 235 shown in FIG. 2 that removes words, connected spaces, and punctuation that are not used to identify food to produce parsed cleaned text. FIG. 6 shows that the parsed text without a food quantity numeric value (QN) and a food quantity unit (QU) ($PT_{WNU}$) enters the food text cleaning algorithm 235 and is analyzed at 612 to determine if any connected spaces (CS) are found; if present, the system then removes all spaces except one space from each set of connected spaces (i.e., a space symbol followed by one or more space symbol) (CS) in process 620 of FIG. 6. If connected spaces are not found or the $PT_{WNU}$ has been through process 620 of FIG. 6, the system then determines at 622 if the $PT_{WNU}$ has any extraneous punctuation (PM) such as periods, question marks, underscores, dashes and symbols not used in the food names; if present, the system removes any such PM from the $PT_{WNU}$ in process 630 of FIG. 6. If PM are not found or the $PT_{WNU}$ has been through process 630 of FIG. 6, the system then determines at 632 if the $PT_{WNU}$ has any specific conjunctions and/or prepositions at the beginning of each segment of $PT_{WNU}$ (CP); if present, the system removes any such CP from $PT_{WNU}$ in process 640 of FIG. 6. If CP are not found or the $PT_{WNU}$ has been through process 640 of FIG. 6, then the $PT_{WNU}$ is equal to the parsed and cleaned text (PCT).

Figure 7:
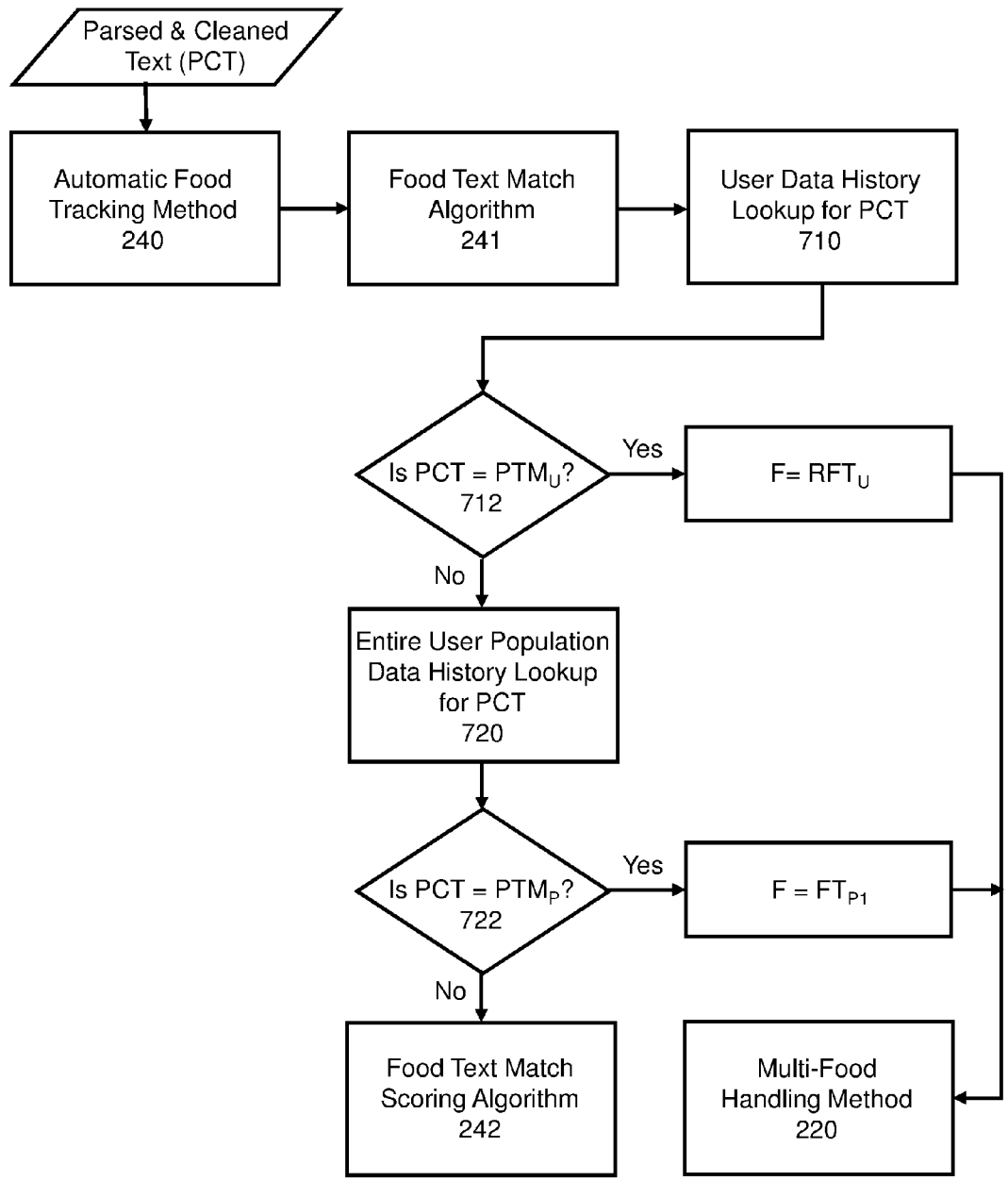
FIG. 7 is a flow diagram showing the steps performed by an embodiment of an automatic food tracking method, including the food text match algorithm, shown in FIG. 2.

The following is a description of an embodiment of the food text cleaning algorithm 235:

i. Run $PT_{WNU}$ through food name aliasing system;
If $PT_{WNU}$ has CS, Then remove from $PT_{WNU}$ all spaces except one space from each CS;
If $PT_{WNU}$ has PM, Then remove PM from $PT_{WNU}$;
If the $PT_{WNU}$ has CP, Then remove CP from $PT_{WNU}$;
$PT_{WNU}$=PCT.

ii. Definitions of terms are:
a. $PT_{WNU}$=parsed text (PT) that has had the food quantity numeric value (QN) and food quantity unit (QU), if any, removed
b. CS=connected spaces in $PT_{WNU}$
c. PM=all periods, question marks, underscores, dashes and symbols not used in the food names in $PT_{WNU}$
d. CP=specific conjunctions and/or prepositions at the beginning of each $PT_{WNU}$ segment
e. PCT=parsed text without food quantity numeric value (QN) and food quantity unit (QU) ($PT_{WNU}$) that has been cleaned by the food text cleaning algorithm FIG. 7 is a flow diagram showing the steps performed by a preferred embodiment of the food text match algorithm 241 as part of the automatic food tracking method 240 shown in FIG. 2. The purpose of the automatic food tracking method 240 is to find and track the food in each parsed and cleaned text (PCT) segment. FIG. 7 shows that the food text match algorithm 241 first runs a user data history lookup on the parsed and cleaned text (PCT) for previous matches for such user ($PTM_U$) 710; if matches are found at 712, then the food to be tracked (F) is set equal to the most recent food tracked for submission $PTM_U$ ($RFT_U$) and such food to be tracked (F) is sent to the multi-food handling method 220. If a match is not found, then an entire user data history lookup for previous matches of the parsed and cleaned text (PCT) is performed using data from the entire user population ($PTM_P$) 720; if matches are found, then the food to be tracked (F) is the food tracked most often by the entire user population for submission $PTM_P$ ($FT_{P1}$) and such food to be tracked (F) is sent to the multi-food handling method 220. If a match is not found at 722, the process moves to the food text match scoring algorithm.

Figure 8:
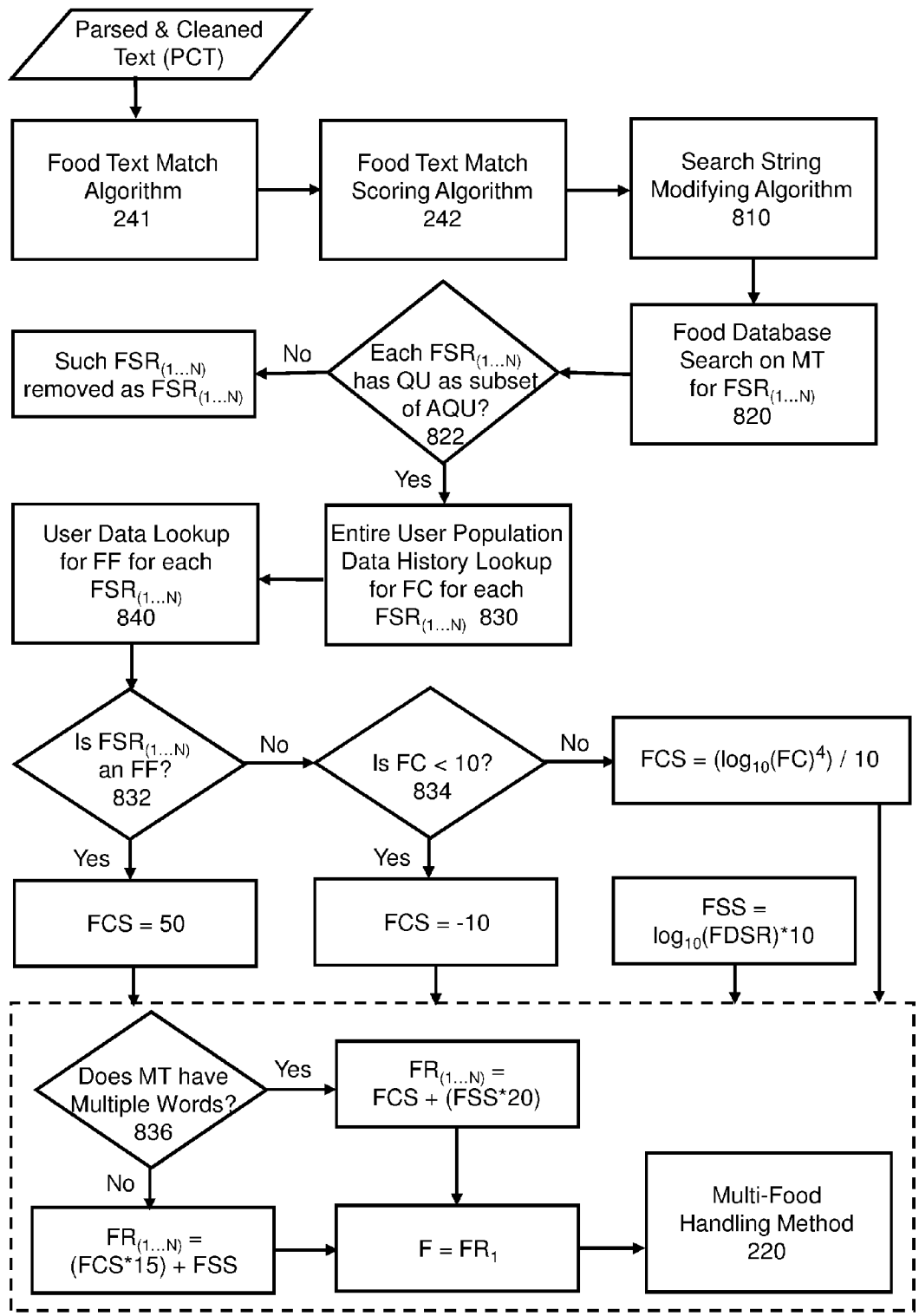
FIG. 8 is a flow diagram showing the steps performed by an embodiment of a food text match scoring algorithm shown in FIG. 2.

The following is a description of an embodiment of the food text match algorithm 241:
  i. Run user data history lookup for PCT;
     If PCT=$PTM_U$, Then F=$RFT_U$;
     If PCT≠$PTM_U$; run entire user population data history lookup for PCT;
     If PCT=$PTM_P$, Then F=$FT_{P1}$;
     Else GoTo food text match scoring algorithm.
  ii. Definitions of terms are:
     a. PCT=parsed text without food quantity numeric value (QN) and food quantity unit (QU) ($PT_{WNU}$) that has been cleaned by the food text cleaning algorithm
     b. F=food to be tracked by system
     c. $PTM_U$=previous PCT matches for a user
     d. RFT=most recent food tracked for submission $PTM_U$ by the user
     e. $PTM_P$=previous PCT matches for the entire user population
     f. $FT_{P1}$=food tracked most often by entire user population for submission $PTM_P$ FIG. 8 is a flow diagram illustrating the steps performed by a preferred embodiment of the food text match scoring algorithm 242 as part of the automatic food tracking method 240 shown in FIG. 2. FIG. 8 shows parsed and cleaned text (PCT) entering through the food text match algorithm 241 and into the food text match scoring algorithm 242. The parsed and cleaned text (PCT) first runs through the search string modifying algorithm 810 which creates modified PCT (MT). A food database fuzzy search on the modified PCT (MT) 820 is then run that generates food database fuzzy search results for foods in relation to MT ($FSR_{(1 \ldots N)}$). The $FSR_{(1 \ldots N)}$ are analyzed at 822 to determine if each $FSR_{(1 \ldots N)}$ has the food quantity unit (QU) for the applicable parsed and cleaned text (PCT) among all food quantity units associated with each $FSR_{(1 \ldots N)}$ (AQU). If a $FSR_{(1 \ldots N)}$ does not have a QU that is a subset of AQU, then such $FSR_{(1 \ldots N)}$ is removed as a $FSR_{(1 \ldots N)}$. If a $FSR_{(1 \ldots N)}$ has a QU that is a subset of AQU, then an entire user population data history lookup is run to find the lifetime total count for number of times each $FSR_{(1 \ldots N)}$ has been tracked by the system (FC) 830. A user data history lookup is also run to find each food denoted a "favorite food" (FF) for each $FSR_{(1 \ldots N)}$ 840 in relation to such user. If at 832 a $FSR_{(1 \ldots N)}$ is a FF, then the food tracking count score for each $FSR_{(1 \ldots N)}$ in relation to such user (FCS) is set equal to 50. If $FSR_{(1 \ldots N)}$ is not a FF, then at 834 if the lifetime total count for number of times each $FSR_{(1 \ldots N)}$ has been tracked by the system (FC) is less than 10, then FCS is set equal to −10. If $FSR_{(1 \ldots N)}$ is not a FF and FC is 10 or greater, then FCS=$(\log_{10}(FC)^4)/10$. The food search score (FSS) for each $FSR_{(1 \ldots N)}$ is determined by the following formula: FSS=$\log_{10}(FDSR)*10$; where FDSR is the food database fuzzy search ranking number for each $FSR_{(1 \ldots N)}$. Lastly, the algorithm determines the food text match scoring rank for each $FSR_{(1 \ldots N)}$ ($FR_{(1 \ldots N)}$). If at 836 the modified PCT (MT) contains more than one word, then $FR_{(1 \ldots N)}$=FCS+(FSS*20); otherwise, if MT contains only one word, then $FR_{(1 \ldots N)}$=(FCS*15)+FSS. The food to be tracked (F) is equal to $FR_1$ (e.g. the top ranked food), and such food to be tracked (F) is sent to the multi-food handling method 220.

Figure 9:
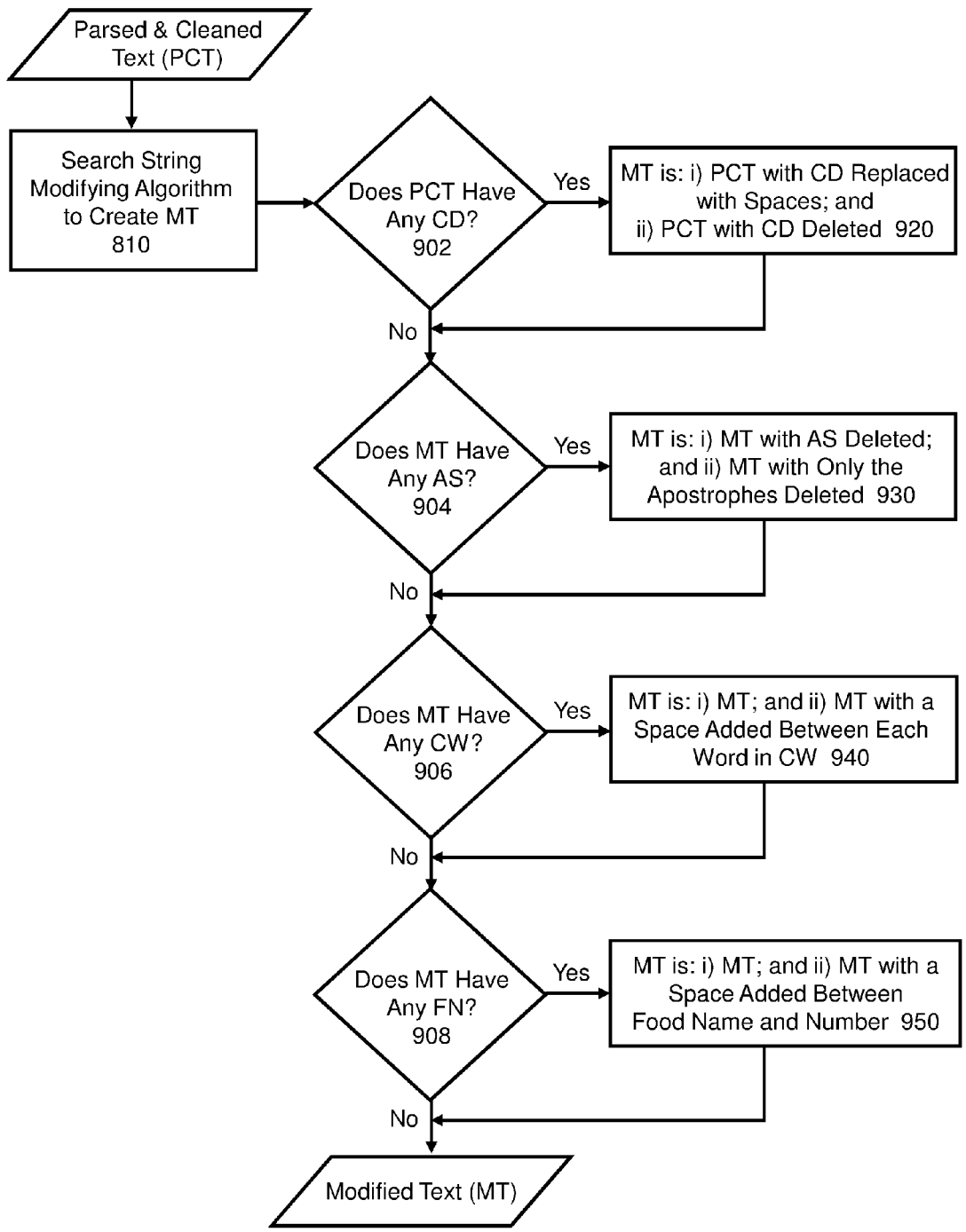
FIG. 9 is a flow diagram showing the steps performed by an embodiment of a search string modifying algorithm shown in FIG. 8.

The following is a description of an embodiment of the food text match scoring algorithm 242:
  i. Run PCT through the search string modifying algorithm to create MT.
     Run food database fuzzy search on MT for $FSR_{(1 \ldots N)}$;
     If QU is not a subset of AQU for each $FSR_{(1 \ldots N)}$, then such $FSR_{(1 \ldots N)}$ is removed as a $FSR_{(1 \ldots N)}$;
     Run entire user population data history lookup for FC for each $FSR_{(1 \ldots N)}$.
     Run user data history lookup for FF for each $FSR_{(1 \ldots N)}$ for such user.
     If $FSR_{(1 \ldots N)}$ is an FF, Then FCS=50;
     Else, If FC<10, Then FCS=−10;
     Else, FCS=$(\log_{10}(FC)^4)/10$.
     FSS=$\log_{10}(FDSR)*10$.
     If MT has multiple words, Then $FR_{(1 \ldots N)}$=FCS+(FSS*20);
     Else, $FR_{(1 \ldots N)}$=(FCS*15)+FSS.
     F=$FR_1$.
  ii. Definitions of terms:
     a. PCT=parsed text without food quantity numeric value (QN) and food quantity unit (QU) ($PT_{WNU}$) that has been cleaned by the food text cleaning algorithm
     b. MT=the modified PCT resulting from the search string modifying system
     c. $FSR_{(1 \ldots N)}$=food database fuzzy search results for foods in relation to MT
     d. QU=food quantity unit
     e. AQU=all food quantity units associated with each food
     f. FCS=food tracking count score for each $FSR_{(1 \ldots N)}$
     g. FC=lifetime total count for number of times each $FSR_{(1 \ldots N)}$ has been tracked by system
     h. FF=food is a user denoted "favorite food"
     i. FSS=food search score
     j. FDSR=food database fuzzy search ranking number for each $FSR_{(1 \ldots N)}$
     k. $FR_{(1 \ldots N)}$=a food and its associated food text match scoring rank (e.g. $FR_1$ is the highest scoring food)
     l. F=food to be tracked by system FIG. 9 is a flow diagram illustrating the steps performed by a preferred embodiment of the search string modifying algorithm 810 as part of the food text match scoring algorithm 242 shown in FIG. 8. FIG. 9 shows parsed and cleaned text (PCT) entering the algorithm, which may first determine at 902 if the PCT has any connecting dashes between words in PCT (CD). If PCT has connecting dashes between words in PCT (CD), then at 920 it may be determined that the modified PCT (MT) is: i) PCT with CD replaced with spaces, and ii) PCT with CD deleted. If PCT does not have any CD or PCT has run through the process at 920 in FIG. 9, then at 904 if MT has an apostrophe followed by an "s" ('s) (AS), then at 930 it may be determined that the MT is: i) MT with any AS deleted, and ii) MT with only the apostrophes deleted. If MT does not have any AS or MT has run through the process at 930 in FIG. 9, then at 906 if MT has multiple words connected with no space in between (CW), then at 940 it may be determined that MT is: i) MT, and ii) MT with a space added between each word in such CW. If MT does not have any CW or MT has run through the process at 940 in FIG. 9, then if MT has food name with a connected number (FN), then at 950 it may be determined that MT is: i) MT, and ii) MT with a space added between the food name and the number, irrespective of the order. If MT at 908 does not have any FN, or MT has run through the process 950 in FIG. 9, then MT is equal to MT.

The following is a description of an embodiment of the search string modifying algorithm 810:
  i. If PCT has CD, Then MT is: i) PCT with CD replaced with spaces, and ii) PCT with CD deleted;
      If MT has AS, Then MT is: i) MT with any AS deleted, and ii) MT with only the apostrophes deleted;
      If MT has CW, Then MT is: i) MT, and ii) MT with a space added between each word in such CW;
      If MT has FN, Then MT is: i) MT, and ii) MT with a space added between the food name and the number, irrespective of the order;
      Else, MT=MT.
  ii. Definitions of terms are:
      a. PCT=parsed text without food quantity numeric value (QN) and food quantity unit (QU) ($PT_{WNU}$) that has been cleaned by the food text cleaning algorithm
      b. CD=connecting dashes between words in PCT
      c. MT=the modified PCT resulting from the search string modifying system
      d. AS=an apostrophe followed by an "s" ('s)
      e. CW=multiple words connected with no space in between
      f. FN=food name with a connected number FIG. 10 is a flow diagram illustrating the steps performed by a preferred embodiment of the location-based food availability algorithm 310 as part of the location-based diet recommendations system 123 shown in FIG. 3. FIG. 10 shows food recommendation request text (FRR) entering the algorithm, which may first determine at 1002 if the FRR has any meal type (MTP) (e.g. breakfast, lunch, dinner or snack) listed in the FRR. The system utilizes fuzzy search logic and word aliases (e.g. "brunch" may be aliased to "lunch") in the process of matching any part of FRR with a meal type (MTP). If FRR does contain a meal type (MTP), then the MTP is equal to the first MTP listed in the food recommendation request text (FRR); otherwise, if the time-of-day (TOD) is earlier than 10:31:00, as may be determined at 1004, then MTP is equal to breakfast (BKF). If the TOD is later than or equal to 10:31:00 and earlier than 15:31:00, as may be determined at 1006, then MTP is equal to lunch (LCH); otherwise, MTP is equal to dinner (DNR). The system next gets at 1010 the global positioning system (GPS) coordinates (GPSC) of the user interface device 110 and then runs the distance calculations for restaurant distances ($RD_{(1\ldots N)}$), in meters, between GPSC and the GPS coordinates of each restaurant in the restaurant database, where $RD_1$ is the closest restaurant to the user's GPSC location. If $RD_{(1\ldots N)}$ is less than or equal to 100 meters, as may be determined at 1022, then the system finds at 1030 the restaurant food menu $RM_{(1\ldots N)}$ for restaurants $R_{(1\ldots N)}$ for each such $RD_{(1\ldots N)}$; otherwise, the system finds at 1040 the $RM_{(1\ldots N)}$ for restaurants $R_{(1\ldots N)}$ that have the three (3) shortest $RD_{(1\ldots N)}$. The system then runs a database search at 1050 for the foods available in $RM_{(1\ldots N)}$ ($FA_{(1\ldots N)}$) for the applicable $RM_{(1\ldots N)}$ and filters the $FA_{(1\ldots N)}$ for MTP matches at 1060. $FA_{(1\ldots N)}$ may consist of one food or meal, which may be a combination of foods.

The following is a description of an embodiment of the location-based food availability algorithm 310:
  i. If FRR text contains MTP, Then MTP=first MTP in FRR;
     Else, if TOD<10:31:00, Then MTP=BKF;
     If 10:31:00<=TOD<15:31:00, Then MTP=LCH;
     Else, MTP=DNR.
     Get GPSC from user interface device;
     Run distance calculation process of GPSC relative to restaurant data GPS coordinates to find $RD_{(1\ldots N)}$;
     If $RD_{(1\ldots N)}$<=100, Then find $RM_{(1\ldots N)}$ for all associated $R_{(1\ldots N)}$;
     Else, find $RM_{(1\ldots N)}$ for $R_{(1\ldots N)}$ for 3 shortest $RD_{(1\ldots N)}$,
     Run food database search for $FA_{(1\ldots N)}$ for $RM_{(1\ldots N)}$,
     Filter for $FA_{(1\ldots N)}$ for MTP matches.
  ii. Definitions of terms are:
      a. FRR=the food recommendation request text submitted, if any, by the user
      b. TOD=time of day
      c. MTP=meal type: breakfast, lunch, dinner or snack
      d. BKF=breakfast meal type
      e. LCH=lunch meal type
      f. DNR=dinner meal type
      g. GPSC=user interface device Global Positioning System (GPS) coordinates
      h. $RD_{(1\ldots N)}$=restaurant distances, in meters, between GPSC and GPS coordinates of each restaurant in the restaurant database, where $RD_1$ is the closest restaurant to the user's GPSC location
      i. $R_{(1\ldots N)}$=restaurant associated with each distance $RD_{(1\ldots N)}$
      j. $RM_{(1\ldots N)}$=restaurant food menu for each $R_{(1\ldots N)}$
      k. $FA_{(1\ldots N)}$=foods available in $RM_{(1\ldots N)}$ FIG. 11 is a flow diagram illustrating the steps performed by a preferred embodiment of the food recommendation algorithm 320 as part of the location-based diet recommendations system 123 shown in FIG. 3. FIG. 11 shows that the algorithm first does a user nutrient data lookup at 1110 for the user's daily nutrient target amounts ($NT_{(1\ldots N)}$) (e.g. 1500 calories, 100 g protein, etc.), for all nutrients that have targets, and then does a user food tracking nutrient data lookup at 1120 for total daily nutrient data amounts ($NT_{(1\ldots N)}$) for all foods (F) tracked, at a given point of time. $NT_{(1\ldots N)}$ are derived from user preferences either directly or through calculation. At 1122, the algorithm then gets the meal type (MTP) and the foods available in $RM_{(1\ldots N)}$ ($FA_{(1\ldots N)}$) from the location-based food availability algorithm 310. FIG. 11 shows at 1130 the equations for the target calorie amount ($TC_{BFK}$, $TC_{LCH}$, $TC_{DNR}$ and $TC_{SNK}$) for each meal type (MTP) as well the equations for remaining daily calories target amount ($RNT_{CAL}$), at a given point of time, and remaining user daily nutrient target amounts ($RNT_{(1\ldots N)}$), at a given point of time, for all nutrients with targets. If $RNT_{CAL}$ is less than the target calorie amount for a given MTP ($TC_{MTP}$), as may be determined at 1132, then the system delivers an "insufficient calories remaining" message to the user; otherwise, if MTP is equal to breakfast (BKF), as may be determined at 1134, then at 1136 the system finds $FA_{(1\ldots N)}$ where the calorie amounts for a given quantity of $FA_{(1\ldots N)}$ ($FAC_{(1\ldots N)}$) is less than or equal to $TC_{BFK}$. Otherwise, if MTP is equal to lunch (LCH), as may be determined at 1138, then at 1140 the system finds $FA_{(1\ldots N)}$ where $FAC_{(1\ldots N)}$ is less than or equal to $TC_{LCH}$; otherwise, if MTP is equal to dinner (DNR), as may be determined at 1142, then at 1144 the system finds $FA_{(1\ldots N)}$ where $FAC_{(1\ldots N)}$ is less than or equal to $TC_{DNR}$; otherwise, at 1146 the system finds $FA_{(1\ldots N)}$ where $FAC_{(1\ldots N)}$ is less than or equal to $TC_{SNK}$. If all nutrient amounts for a given quantity of $FA_{(1\ldots N)}$ ($FAN_{(1\ldots N)}$), for all nutrients with targets, are less than or equal to the remaining user daily nutrient target amounts ($RNT_{(1\ldots N)}$) for such $FA_{(1\ldots N)}$, as may be determined at 1148, then the food/meal recommendation (FR) is a $FA_{(1\ldots N)}$ selected by the user from a randomly ordered list, except that any $FA_{(1\ldots N)}$ that are user "favorite foods" (FF) are listed first.

The following is a description of an embodiment of the food recommendation algorithm 320:

i. Run user nutrient target data lookup for $NT_{(1...N)}$;
  Run user food tracking nutrient data lookup for $ND_{(1...N)}$;
  Get MTP and $FA_{(1...N)}$ from the location-based food availability algorithm;
  $TC_{BFK}=(NT_{CAL}-(NT_{CAL}*0.10*TS))*0.25$
  $TC_{LCH}=(NT_{CAL}-(NT_{CAL}*0.10*TS))*0.35$
  $TC_{DNR}=(NT_{CAL}-(NT_{CAL}*0.10*TS))*0.40$
  $TC_{SNK}=NT_{CAL}*0.10$
  $RNT_{CAL}=NT_{CAL}-ND_{CAL}$
  $RNT_{(1...N)}=NT_{(1...N)}-ND_{(1...N)}$;
  If $RNT_{CAL}<TC_{MTP}$, Then deliver "insufficient calories remaining for food recommendations" message to user.
  Else, $RNT_{CAL}>=TC_{MTP}$,
    Then, If MTP=BKF find $FA_{(1...N)}$ where $FAC_{(1...N)}<=TC_{BFK}$;
    Else If MTP=LCH find $FA_{(1...N)}$ where $FAC_{(1...N)}<=TC_{LCH}$;
    Else If MTP=DNR find $FA_{(1...N)}$ where $FAC_{(1...N)}<=TC_{DNR}$;
    Else, MTP=SNK and find $FA_{(1...N)}$ where $FAC_{(1...N)}<=TC_{SNK}$;
  Then, If all $FAN_{(1...N)}<=RNT_{(1...N)}$ for $FA_{(1...N)}$, Then FR=user selected $FA_{(1...N)}$ from a randomly ordered list, except that any $FA_{(1...N)}$ that are FF are listed first;
  Else, deliver "no foods comply with all nutrient limits" message to user.

ii. Definitions of terms are:
   a. $NT_{(1...N)}$=user daily nutrient target amounts (e.g. 1500 calories, 100 g protein, etc.) for all nutrients that have targets
   b. $ND_{(1...N)}$=total daily nutrient data amounts for all foods (F) tracked, at given point of time
   c. MTP=meal type: breakfast, lunch, dinner or snack
   d. $TC_{MTP}$=target calorie amount for a given MTP (e.g. $TC_{BFK}$, $TC_{LCH}$, $TC_{DNR}$, $TC_{SNK}$)
   e. $TC_{BFK}$=target calorie amount for a breakfast MTP
   f. $TC_{LCH}$=target calorie amount for a lunch MTP
   g. $TC_{DNR}$=target calorie amount for a dinner MTP
   h. $TC_{SNK}$=target calorie amount for a snack MTP
   i. $RNT_{CAL}$=remaining daily calories target amount, at given point of time
   j. $RNT_{(1...N)}$=remaining user daily nutrient target amounts, at given point of time for all nutrients with targets
   k. $NT_{CAL}$=user daily calorie target
   l. $ND_{CAL}$=total daily calories data amount for all foods (F) tracked at given point of time
   m. BKF=breakfast meal type
   n. LCH=lunch meal type
   o. DNR=dinner meal type
   p. SNK=snack meal type
   q. TS=user number of snacks preference (e.g. 1, 2, 3 or 4)
   r. $FA_{(1...N)}$=foods available in $RM_{(1...N)}$
   s. $FAC_{(1...N)}$=calorie amounts for a given quantity of $FA_{(1...N)}$
   t. $FAN_{(1...N)}$=nutrient amounts for a given quantity of $FA_{(1...N)}$ for all nutrients with targets
   u. FR=food/meal recommendation
   v. FF=food is a user denoted "favorite food"

While the foregoing has been with reference to preferred embodiments, it will be appreciated that changes may be made from these embodiments without departing from the principles of the invention, the scope of which is defined by the appended claims.

The invention claimed is:

1. A computer-implemented method of automatic diet tracking, comprising:
   receiving text from a user that describes a food that is to be tracked;
   parsing the received text into text segments;
   identifying automatically in each parsed text segment a food quantity value and a food quantity unit for said food that is to be tracked, said identifying comprising searching said parsed text segment for a quantity value followed directly by a quantity unit, and assigning said quantity value and said quantity unit to be said food quantity value and said food quantity unit for the food to be tracked, and upon not finding a quantity value followed directly by a quantity unit, selecting as said food quantity value and said food quantity unit a most frequently occurring quantity value and quantity unit for said food to be tracked;
   cleaning the parsed text segments to identify and remove words, connected spaces, and punctuation that are not used to identify food to produce parsed cleaned text;
   processing the parsed cleaned text segments using a text match algorithm to find said food that is to be tracked in each parsed cleaned text segment comprising ranking each food text match found using a ranking process, and selecting the food with a predetermined rank to be the food that is to be tracked; and
   reporting diet tracking information for said food to be tracked.

2. The method of claim 1, wherein said parsing further comprises removing all quantity values and quantity units from said parsed text segments, and wherein said ranking said found food text matches comprises searching a past history of said user for previous matches, and selecting from said past history a most recent food tracked as said food to be tracked.

3. The method of claim 2, wherein upon a food match not being found in said searching, then searching a user population history for previous matches, and selecting a food that has been most often tracked as said food to be tracked.

4. The method of claim 3, wherein upon a food match not being found in said user population history, processing said parsed text using a search string modifying algorithm to create a modified text string; performing a fuzzy search on a food database for food results relevant to said modified text string; scoring said food results to create a food text match score; and selecting as said food to be tracked a food having the top score.

5. The method of claim 4, wherein said scoring comprises determining from a user data history lookup for said user whether a food of said food results is designated as a favorite food of said user, and, if so, scoring that food to have the highest score, otherwise, upon no favorite food designation being found, determining from an entire user population history a total count for a number of times each food has been tracked, and scoring the food with the highest count as the food with the highest score.

6. The method of claim 4, wherein said search string modifying algorithm creates said modified search string by performing one or more of: (i) removing, or replacing with spaces, connecting dashes between words, if any, (ii) removing an apostrophe followed by a letter "s" and removing an apostrophe only, if any, and (iii) inserting a space between connected words and numbers that have no space, if any.

7. The method of claim 1, wherein said searching for a food quantity value and a food quantity unit comprises performing a fuzzy logic search of said parsed text for a written number or a numeric value, and upon finding said written number or numeric value, performing a further fuzzy logic search of said parsed text for a match of a quantity unit term directly following said written number or numeric quantity and, if found, assigning said written number or numeric quantity to said food quantity value and assigning said quantity unit term to said food quantity unit.

8. The method of claim 7, wherein upon not finding said written number or numeric quantity, performing a further fuzzy logic search of said parsed text for a match of a quantity unit term, and, if found, assigning said quantity unit term to said food quantity unit, and, if not found, searching a user data history for said user for a most recently tracked food quantity unit for said food to be tracked, and setting the food quantity unit for said food to be tracked to be the most recently tracked food quantity unit.

9. The method of claim 8, wherein upon not finding a most recently tracked food quantity unit in said user data history, searching an entire user population history for a most frequently tracked food quantity unit for said food to be tracked, and setting said food quantity unit for the food to be tracked to be said most frequently tracked food quantity unit.

10. The method of claim 1 further comprising providing diet recommendations based upon food availability within a predetermined distance of a location of said user and target nutrient values of said user.

11. Non-transitory computer readable media embodying executable instructions for controlling a computer for an automatic diet tracking method, comprising:
receiving text from a user that describes a food that is to be tracked;
parsing the received text into text segments;
identifying automatically in each parsed text segment a food quantity value and a food quantity unit for said food that is to be tracked, said identifying comprising searching said parsed text segment for a quantity value followed directly by a quantity unit, and assigning said quantity value and said quantity unit to be said food quantity value and said food quantity unit for the food to be tracked, and upon not finding a quantity value followed directly by a quantity unit, selecting as said food quantity value and said food quantity unit a most frequently occurring quantity value and quantity unit for said food to be tracked;
cleaning the parsed text segments to identify and remove words, connected spaces, and punctuation that are not used to identify food and produce parsed cleaned text;
processing the parsed cleaned text segments using a text match algorithm to find said food that is to be tracked in each parsed cleaned text segment comprising ranking each food text match found using a ranking process, and selecting the food with a predetermined rank to be the food that is to be tracked; and
reporting diet tracking information for said food to be tracked.

12. The non-transitory computer readable media of claim 11, wherein said parsing further comprises removing all quantity values and quantity units from said parsed text segments, and wherein said ranking said found food text matches comprises searching a past history of said user for previous matches, and selecting from said past history a most recent food tracked as said food to be tracked.

13. The non-transitory computer readable media of claim 12, wherein upon a food match not being found in said searching, then searching a user population history for previous matches, and selecting a food that has been most often tracked as said food to be tracked.

14. The non-transitory computer readable media of claim 13, wherein upon a food match not being found in said user population history, processing said parsed cleaned text using a search string modifying algorithm to create a modified text string; performing a fuzzy search on a food database for food results relevant to said modified text string; scoring said food results to create a food text match score; and selecting as said food to be tracked a food having the top score.

15. The non-transitory computer readable media of claim 14, wherein said scoring comprises determining from a user data history lookup for said user whether a food of said food results is designated as a favorite food of said user, and, if so, scoring that food to have the highest score, otherwise, upon no favorite food designation being found, determining from an entire user population history a total count for a number of times each food has been tracked, and scoring the food with the highest count as the food with the highest score.

16. The non-transitory computer readable media of claim 14, wherein said search string modifying algorithm creates said modified search string by performing one or more of: (i) removing, or replacing with spaces, connecting dashes between words, if any, (ii) removing an apostrophe followed by a letter "s" and removing an apostrophe only, if any, and (iii) inserting a space between connected words and numbers that have no space, if any.

17. The non-transitory computer readable media of claim 11, wherein said searching for a food quantity value and a food quantity unit comprises performing a fuzzy logic search of said parsed text for a written number or a numeric value, and upon finding said written number or numeric value, performing a further fuzzy logic search of said parsed text for a match of a quantity unit term directly following said written number or numeric quantity and, if found, assigning said written number or numeric quantity to said food quantity value and assigning said quantity unit term to said food quantity unit.

18. The non-transitory computer readable media of claim 17, wherein upon not finding said written number or numeric quantity, performing a further fuzzy logic search of said parsed text for a match of a quantity unit term, and, if found, assigning said quantity unit term to said food quantity unit, and, if not found, searching a user data history for said user for a most recently tracked food quantity unit for said food to be tracked, and setting the food quantity unit for said food to be tracked to be the most recently tracked food quantity unit.

19. The non-transitory computer readable media of claim 18, wherein upon not finding a most recently tracked food quantity unit in said user data history, searching an entire user population history for a most frequently tracked food quantity unit for said food to be tracked, and setting said food quantity unit for the food to be tracked to be said most frequently tracked food quantity unit.

20. The non-transitory computer readable media of claim 11 further comprising providing diet recommendations based food availability within a predetermined distance of a location of said user and target nutrient values of said user.

* * * * *